(12) United States Patent
Gawhega

(10) Patent No.: US 11,672,893 B1
(45) Date of Patent: Jun. 13, 2023

(54) AIRLESS DUAL RESERVOIR SYSTEM FOR CONNECTION TO AND USE WITH A BREAST PUMP

(71) Applicant: Victoria C. Gawhega, Stillwater, OK (US)

(72) Inventor: Victoria C. Gawhega, Stillwater, OK (US)

(*) Notice: Subject to any disclaimer, the term of this patent is extended or adjusted under 35 U.S.C. 154(b) by 271 days.

(21) Appl. No.: 17/090,581

(22) Filed: Nov. 5, 2020

Related U.S. Application Data

(60) Provisional application No. 62/930,894, filed on Nov. 5, 2019.

(51) Int. Cl.
*A61M 1/06* (2006.01)

(52) U.S. Cl.
CPC .................. *A61M 1/068* (2014.02)

(58) Field of Classification Search
CPC ................ A61M 1/068; A61M 1/06
See application file for complete search history.

(56) References Cited

FOREIGN PATENT DOCUMENTS

WO    WO-2016024558 A1 * 2/2016 .............. A61M 1/06

* cited by examiner

*Primary Examiner* — Amber R Stiles
(74) *Attorney, Agent, or Firm* — GableGotwals

(57) ABSTRACT

Embodiments of a breast feeding apparatus include a breast pump end configured for connection to a breast pump; a nipple end configured for connection to a nipple; a first sized reservoir and a second sized reservoir having a size different from that of the first sized reservoir located between the breast pump end and the nipple end; tubing connecting the breast pump end to the first sized and second different sized reservoirs, and nipple end to one another in series; and a plurality of air release valves located along the tubing. A method of using the breast feeding apparatus includes connecting the breast pump end of the apparatus to a breast pump, activating the breast pump to pump breast milk into the tubing and reservoirs of the apparatus, and releasing air through one or more of the air release valves. The air release may be manual or automatic.

2 Claims, 3 Drawing Sheets

AIRLESS DUAL RESERVOIR SYSTEM FOR CONNECTION TO AND USE WITH A BREAST PUMP

CROSS-REFERENCE TO RELATED APPLICATIONS

This application claims priority to U.S. Provisional Application No. 62/930,894, filed Nov. 5, 2019.

BACKGROUND

This disclosure is in the field of breast pumps and, in particular, to devices and systems that connect to a breast pump and facilitate nursing of an infant.

SUMMARY

Embodiments of a breast feeding apparatus of this disclosure includes a breast pump end configured for connection to a breast pump; a nipple end configured for connection to a nipple; a first sized reservoir and a second sized reservoir having a size different from that of the first sized reservoir located between the breast pump end and the nipple end; tubing connecting the breast pump end to the first sized and second different sized reservoirs, and nipple end to one another in series; and a plurality of air release valves located along the tubing. Medical grade connectors, tubing and components should be used throughout.

DETAILED DESCRIPTION

Figure 1:
FIG. 1 is a schematic of an embodiment of an airless dual reservoir system of this disclosure.
Figure 4:
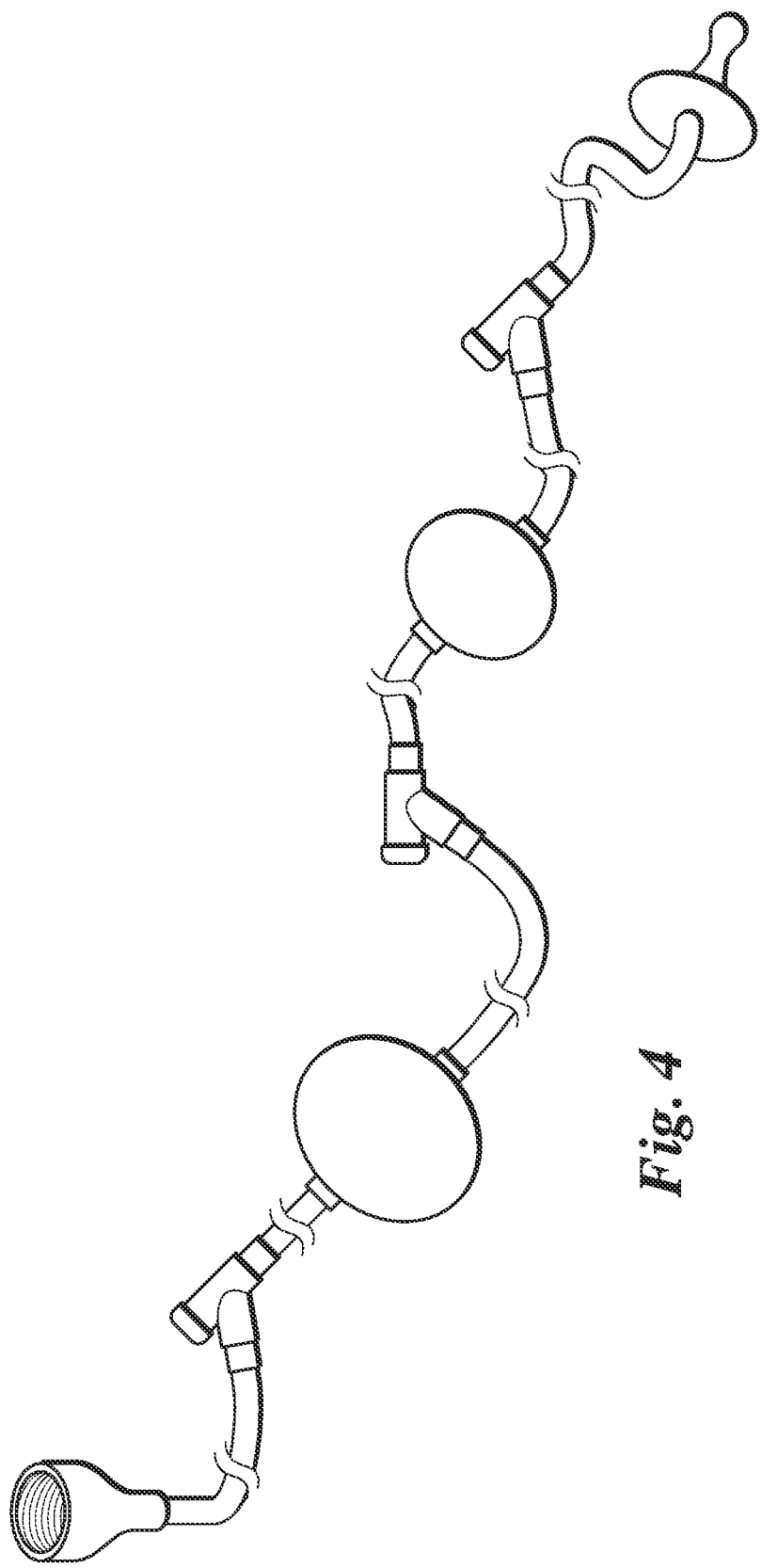
FIG. 4 is schematic of another embodiment of an airless dual reservoir system of this disclosure.
Figure 2:
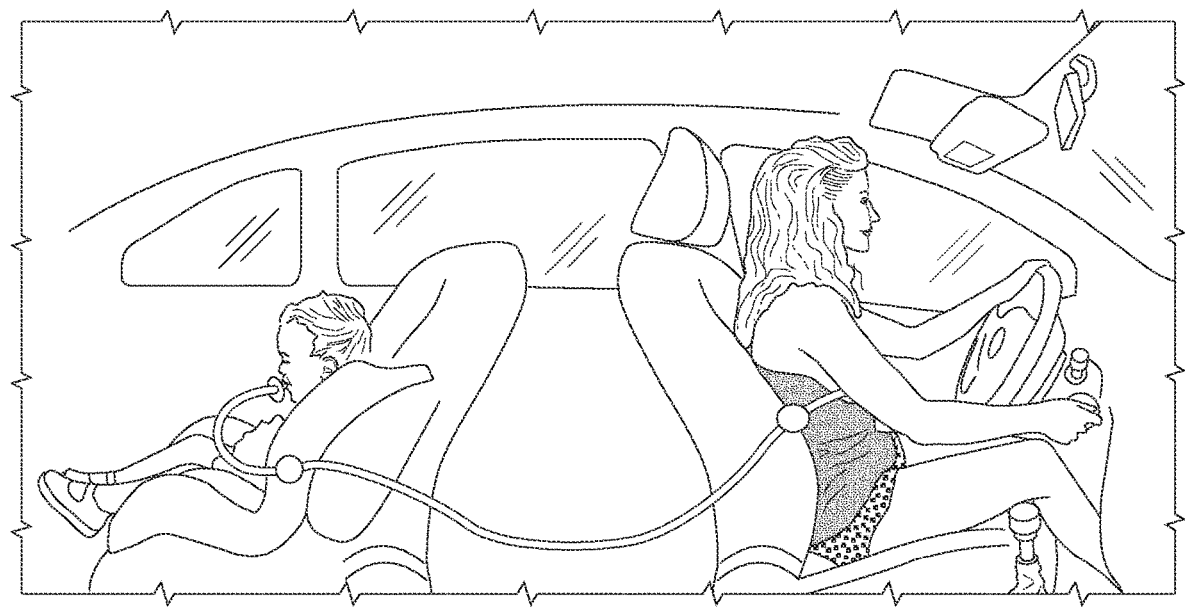
FIG. 2 is an illustration of an embodiment of a system of this disclosure used while traveling.
Figure 7:
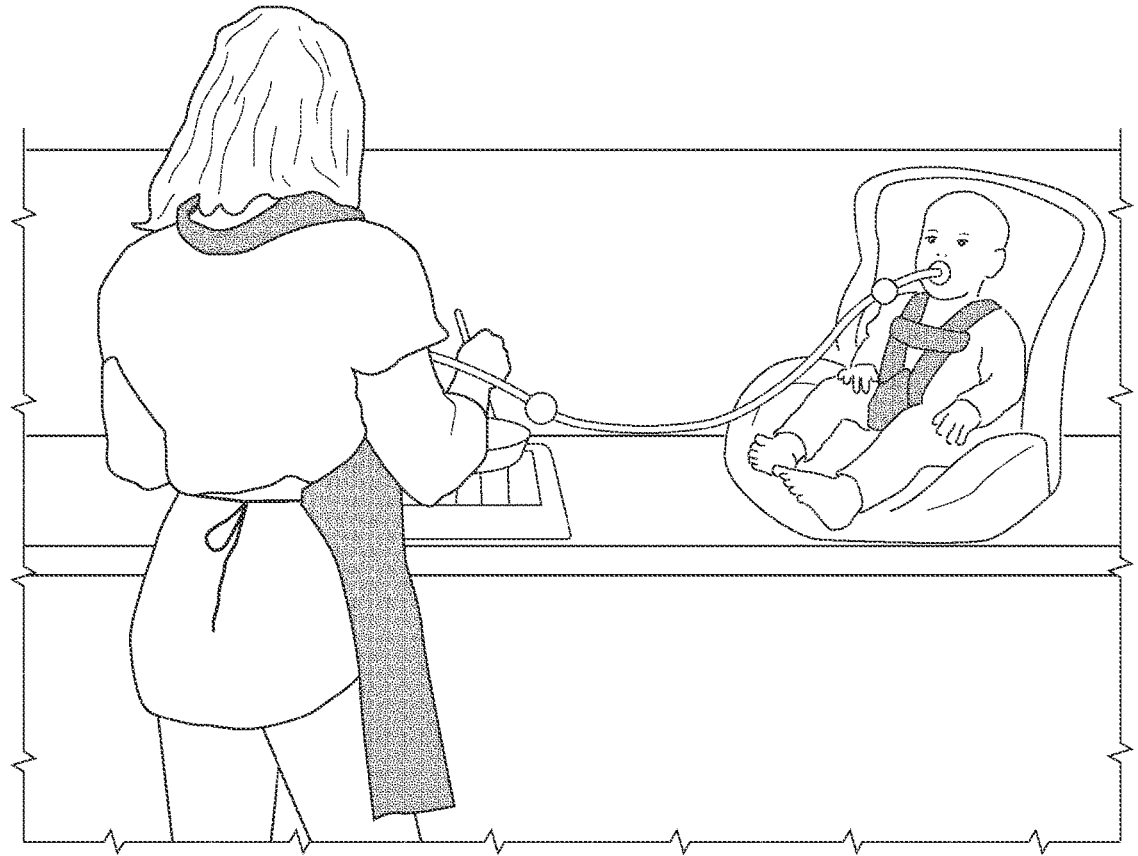
FIG. 7 is an illustration of an embodiment of a system of this disclosure used while during a household chore.
Figure 3:
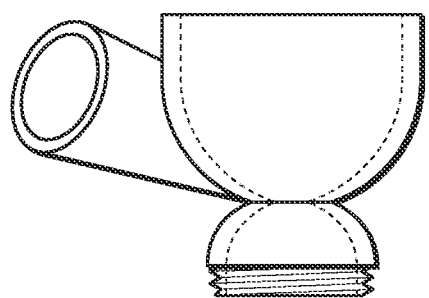
FIG. 3 is a front elevation view of a pump-to-pump connector of this disclosure. A lowermost threaded end of the connector mates to an uppermost threaded end of a pump-to-tube connector. See FIG. 3.
Figure 5:
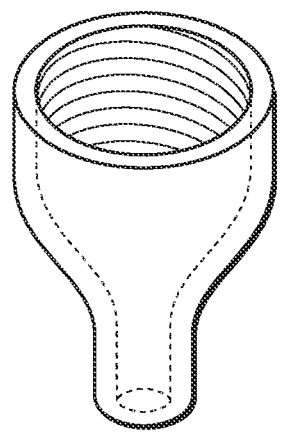
FIG. 5 is an isometric view of an embodiment of a pump-to-tube connector of this disclosure.
Figure 6B:
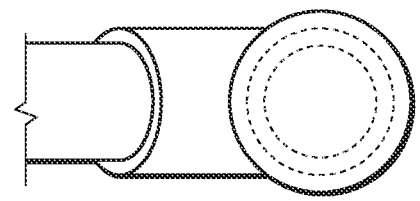
FIG. 6B is a front elevation view of the air release valve of FIG. 6A.
Figure 6C:
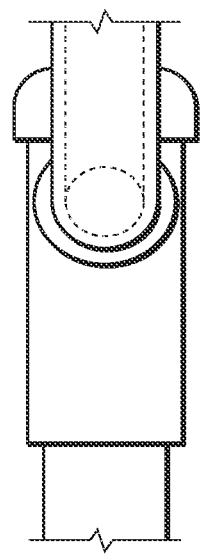
FIG. 6C is a side elevation view of the air release valve of FIG. 6A.
Figure 6A:
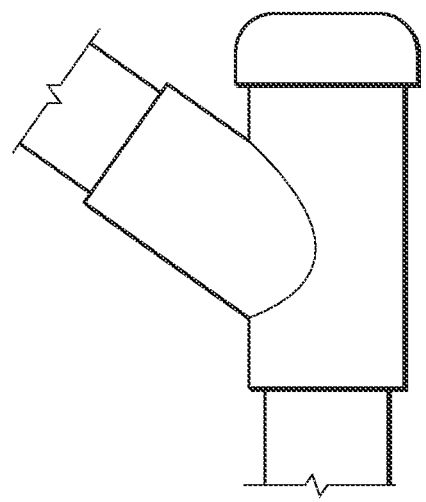
FIG. 6A is a top plan view of an embodiment of an air release valve of this disclosure.

In embodiments of this disclosure, a breast feeding apparatus includes a breast pump end; a nipple end; a first sized reservoir located toward, and downstream of, the breast pump end; a second different sized reservoir located downstream of the first sized reservoir toward, and upstream of, the nipple end; tubing connecting in series the breast pump end, first sized reservoir, second different sized reservoir, and nipple end; and a plurality of air release valves located along the tubing. Medical grade connectors, tubing and components should be used throughout.

A first air release valve of the plurality of air release valves may be located between the breast pump end and the first sized reservoir; a second air release valve of the plurality may be located between the first and second different sized reservoirs; and a third air release valve may be located between the second different sized reservoir and the nipple (baby feeding) end. The first, second, and third release valves each include an inlet end for connection to a corresponding one of the tubing, an outlet end for connection to another corresponding one of the tubing, and a vent end for air to vent external to tubing. The reservoirs may be different sized reservoirs. The reservoirs are sized appropriately for anticipated, normal volumes of breast milk (e.g. a range of ½ oz to 2 oz per pumping session, assuming a range of about 25 oz to 35 oz per 24 hours). The first sized reservoir may be larger in size than the second different sized reservoir. The reservoirs may be disconnected from the apparatus for cleaning, as may other components.

The breast pump end may include a connector configured at one end for connection to a breast pump and at another end for connection to the tubing. The connector may be a two-part connector, with a first part being a breast pump connector and the second part being the tube connector, the first and second parts mating with one another. In other embodiments, the breast pump end may be connected to a source of milk and gravity fed or pumped. The nipple end, when in an intended use, includes a nipple. The nipple end may be a threaded end.

A method of using a breast feeding apparatus of this disclosure includes connecting the breast pump end of the apparatus to a breast pump, activating the breast pump to pump breast milk into the tubing and reservoirs of the apparatus, and releasing air through one or more of the air release valves. The air release may be manual or automatic.

While embodiments of a breast feeding apparatus and method of its use have been described and illustrated, modifications apart from those shown or suggested here may be made without departing from the scope of the following claims. The terms that are employed in the claims draw their meaning from the use of the terms in the specification. The same terms employed in the prior art may be broader in meaning than specifically employed here. Whenever there is a question between the broader definition of such terms used in the prior art and the more specific use of the terms herein, the more specific meaning is meant.

What is claimed:

1. A breast feeding apparatus comprising:
   a breast pump end configured for connection to a breast pump;
   a nipple end configured for connection to a nipple;
   a first sized reservoir and a second different sized reservoir located between the breast pump end and the nipple end;
   tubing connecting the breast pump end, the first sized and second different sized reservoirs, and the nipple end to one another in series;
   and a plurality of air release valves located along the tubing.

2. The breast feeding apparatus of claim 1, further comprising, a first air release valve of the plurality located between the breast pump end and the first sized reservoir, a second air release vale of the plurality located between the first sized and second different sized reservoirs, and a third air release valve of the plurality located between the second different sized reservoir and the nipple end, the first, second, and third air release valves including an inlet end for connection to a corresponding one of the tubing, an outlet end for connection to another corresponding one of the tubing, and an air vent end for air to vent external to the tubing.

* * * * *